United States Patent [19]

Kirschke et al.

[11] Patent Number: 5,336,780
[45] Date of Patent: Aug. 9, 1994

[54] 5-AMINO-1-HYDROXIMOYL PYRAZOLES

[75] Inventors: Klaus Kirschke, Eiche; Gerhard Lutze; Ernst Schmitz, both of Berlin; Erich Wolff, Solingen, all of Fed. Rep. of Germany

[73] Assignee: Agfa Gevaert Aktiengesellschaft, Leverkusen, Fed. Rep. of Germany

[21] Appl. No.: 36,962

[22] Filed: Mar. 25, 1993

[30] Foreign Application Priority Data

Apr. 6, 1992 [DE] Fed. Rep. of Germany ....... 4211479

[51] Int. Cl.$^5$ .......................................... C07D 231/38
[52] U.S. Cl. ................................................... 548/371
[58] Field of Search ...................................... 548/371.7

[56] References Cited

FOREIGN PATENT DOCUMENTS 0226849 1/1987 European Pat. Off. ......... 548/371.7

OTHER PUBLICATIONS

J. Abstracts, J61065-247-A, Silver Halide . . . Magenta Coupler, Sep. 1984.
J. Abstracts, J6 3041-851-A, Color Image . . . Coupler, Aug. 1986.
J. Abstracts, J6 3218-665-A, N-(4-Chloropyrazolyl) . . . Couplers, Mar. 1987.

*Primary Examiner*—Robert W. Ramsuer
*Assistant Examiner*—Joseph K. McKane
*Attorney, Agent, or Firm*—Connolly and Hutz

[57] ABSTRACT

Pyrazolo[5,1-c][1,2,4]triazoles of the general formula I

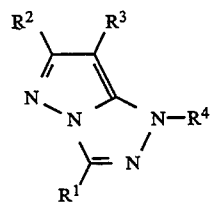

in which
$R^1$ and $R^2$ represent alkyl, cycloalkyl, aralkyl, aryl, alkoxy or heterocyclic radicals, $R^3$ is hydrogen, halogen or an alkyl, cycloalkyl, aralkyl, aryl or heterocyclic radical bonded via a hetero atom, wherein $R^2$ and $R^3$ may be closed to form a ring, and $R^4$ is hydrogen or an acyl radical, are prepared from 3(5)-amino-pyrazoles of the general formula II

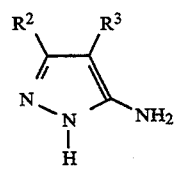

in which $R^2$ and $R^3$ have the abovementioned meaning, by reaction with a hydroximoyl halide of the general formula III

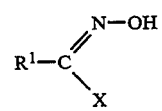

in which $R^1$ has the abovementioned meaning and X represents chlorine or bromine, in the presence of a tertiary base to give a 5-amino-1-hydroximoyl-pyrazole, subsequent reaction with an aliphatic or aromatic sulphonyl chloride in the presence of a tertiary base to give an O-sulphonated 5-amino-1-hydroximoyl-pyrazole, acylation to give an O-sulphonated 5-acylamino-1-hydroximoyl-pyrazole or 5-bisacylamino-1-hydroximoyl-pyrazole and then treatment with bases. The optionally O-sulphonated 5-amino-1-hydroximoyl-pyrazoles or O-sulphonated 5-acylamino- and 5-bisacylamino-1-hydroximoyl-pyrazoles are new valuable intermediates for the synthesis of pyrazolo[5,1-c][1,2,4]-triazoles.

1 Claim, No Drawings

5-AMINO-1-HYDROXIMOYL PYRAZOLES

The invention relates to a new process for the preparation of pyrazolo[5,1-c][1,2,4]triazoles from 1-unsubstituted 3(5)-amino-pyrazoles.

It is known that 2-equivalent purple couplers which are derived from pyrazolo[5,1-c][1,2,4]triazole are used in colour photographic recording materials. Purple couplers of this type have considerable advantages over the hitherto frequently used 2-equivalent purple couplers derived from pyrazolin-5-ones, especially with regard to colour reproduction (J. Chem. Soc. Perkin I, 1977, 2047).

The preparation of pyrazolo[5,1-c][1,2,4]triazole 2-equivalent purple couplers, however, is expensive and associated with considerable difficulties which are partly based on the fact that formation of the bicyclic ring system is complicated and includes reactions which are difficult to control on an industrial scale and which produce low yields. Furthermore, the introduction of the halogen atoms which are eliminated on development of the colour, which is required when preparing 2-equivalent couplers, is complicated because it involves first saponification and decarboxylation and then halogenation. Decarboxlation is also difficult to control on an industrial scale and in many cases dihalogenated products are obtained on halogenation, from which one halogen atom has to be eliminated in a subsequent reaction, e.g. using ascorbic acid or trialkyl phosphite (Synthesis 1985, 299).

It is known that pyrazolo[5,1-c][1,2,4]triazoles may be prepared by ring contraction from 1,2,4-triazolo[3,4-b]-[1,3,4]thiadiazines via sulphur extrusion. The yields, however, are mostly poor [e.g. J. Bailey, J. Chem Soc. Perk. 1 1977, 2047; H. Beyer, G. Wolter and H. Lemke, Chem. Ber. 89, 2550 (1956); Res. Discl. 12443 (1974); EP 285274 (1988)], which restricts general applicability of this method. Another disadvantage of this method is that thiocarbohydrazide or carbon disulphide has to be used as the starting material for the 1,2,4-triazolo[3,4-b]-[1,3,4]thiadiazines (e.g. EP 347235; EP 284240; EP 285274; JP 62 295051; EP 178788; JP 61 260085; JP 61 260072), special safety precautions being required when handling these on an industrial scale. It is also known that 3,4-diamino-1,2,4-triazoles may be cyclo-condensed with β-ketocarboxylic acids, wherein isomeric mixtures of 1,2,4-triazolo[4,3-b][1,2,4]triazepin-6-ones and 1,2,4-triazolo[4,3-b][1,2,4]triazepin-8-ones are produced, of which only the former may be converted into pyrazolo[5,1-c][1,2,4]triazoles by heating in acetanhydride [Gehlen and R. Drohla, Arch. Pharm. 303, 709 (1970); R-M. Claramunt, J. M. Fabrega and J. Elguero, J. Heterocycl. Chem. 11, 751 (1974)]. Furthermore, it is known that pyrazolo[5,1-c][1,2,4]triazoles may be prepared by photolysis of 7-diazo-1,2,4-triazolo[4,3-b]pyridazin-8-ones [H. G. Becker and H. Böttcher, J. Prakt. Chem. 314, 55 (1972); B. Stanovik, M. Tisler, B. Kirn and I. Kovac, J. Heterocycl. Chem. 16, 195 (1975)]. The disadvantage of this method comprises the problems which are linked with an industrial photolysis process. Furthermore, the reaction includes a thermal decarboxylation if it is to produce the 7-unsubstituted pyrazolo[5,1-c][1,2,4]triazole which is important when synthesizing a colour coupler. Decarboxylation is also a disadvantage in numerous other known processes (e.g. WO 8601915; EP 182617; EP 178789; EP 287265; DD 263060; EP 217353; EP 269436; JP 01 233285). 3(5)-amino-pyrazoles are also used as the starting material for the preparation of pyrazolo[5,1-c][1,2,4]triazoles. For instance, 3-acylpyrazolo[5,1-c][1,2,4]triazoles are accessible by diazotisation and coupling with CH acid compounds, such as 2-halo-1,3-dicarbonyl compounds, and subsequent ring-closure [e.g. M. H. Elnagdi, M. R. H. Elmoghayar, E. M. Kandeel and M. K. A. Ibrahim, J. Heterocycl. Chem. 14, 227 (1977); A. G. A. Elagamey, S. Z. A. Sowellim and M. N. Khodeir, Arch. Pharm. Res. 10, 14 (1987); M. H. Elnagdi, E. M. Zayed, M-A. E. Khalifa and S. A. Ghozlan, Monatsh. Chem. 112, 245 (1981)]. The use of phenacyl thiocyanates [A. S. Shawali and M. S. Algharits, J. Heterocycl. Chem. 24, 1341 (1987); A. O. Abdelhamin and A. S. Shawali, Z. Naturforsch. 42b, 613 (1987)] or of nitroalkanes [JP 02 115183] as the CH acid component represents an analogous variant. Disadvantages of these methods are that they are not generally applicable and, as in the case of the 2-halo-1,3-dicarbonyl compounds, lead only to 3-acyl-pyrazolo[5,1-c][1,2,4]triazoles.

Reduction of 3(5)-diazono-pyrazoles produces 3(5)-hydrazino-pyrazoles which, after acylation of the hydrazino group, may be cyclised to give pyrazolo[5,1-c]-[1,2,4]-triazoles. Reduction of the 3(5)-diazono-pyrazoles is usually performed with tin(II) chloride [e.g. DE 3708333; JP 61 249968; JP 61 249969; JP 62 158259], which produces considerable problems with separation and regeneration of the tin oxidation products as well as product isolation [J. De Mendoza and J. M. Garcia-Marquina Rodrigo, Anales de Quimica 66, 911 (1970)]. Cyclisation of the 3(5)-(2-acyl-hydrazino)-pyrazoles is performed by heating with thionyl chloride [e.g. EP 379110; JP 62 033178; JP 62 158283] or phosphorus oxychloride [e.g. EP 217353; JP 61 249987; JP 61 249967; EP 183445], which requires extra technical measures in order to prevent corrosion and protect the environment. Finally, 3(5)-amino-pyrazoles and 3(5)-hydroxy-pyrazoles which are not substituted in the 1-position may be cyclised with hydrazidoyl halides in the presence of tertiary bases with elimination of ammonia or water to give 1-substituted pyrazolo[5,1-c][1,2,4]triazoles [e.g. H. A. Elfahham, F. F. Abdel-Latif and S. K. Mohamed, Indian J. Chem. 29 B, 381 (1990); H. Graf and G. Klebe, Chem. Ber. 120, 965 (1987)]. This method has the disadvantage that only 1-substituted pyrazolo[5, 1-c][1,2,4]triazoles are accessible.

Therefore, the aim of the invention is to develop a process which allows the disadvantages of the known processes to be avoided and permits the preparation of pyrazolo[5,1-c]-[1,2,4]triazoles in industrially simple process steps by using starting materials which are readily available and easy to handle, and which is universally applicable.

The object of the invention is a process for the preparation of pyrazolo[5,1-c][1,2,4]triazoles of the general formula I,

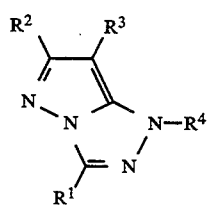

in which $R^1$ and $R^2$ are identical or different optionally substituted radicals and represent alkyl, cycloalkyl, aralkyl, aryl, alkoxy, or heterocyclic radicals, $R^3$ is hydrogen, halogen or an optionally substituted alkyl, cycloalkyl, aralkyl, aryl or heterocyclic radical which is bonded via a hetero atom such as nitrogen, oxygen, sulphur, selenium or phosphorus and wherein $R^2$ and $R^3$ may be closed to form a ring and $R^4$ is hydrogen or an acyl radical, from 3(5)-amino-pyrazoles, characterised by the following sequence of process steps;

a) a 3(5)-amino-pyrazole of the formula II,

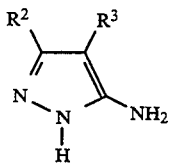

in which $R^2$ and $R^3$ have the stated meanings, is reacted in the presence of a tertiary base with a hydroximoyl halide of the formula III,

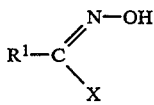

in which $R^1$ has the stated meaning and X represents chlorine or bromine, with the formation of a 5-amino-1-hydoximoyl-pyrazole of the formula IV

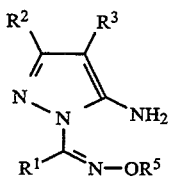

in which $R^1$, $R^2$ and $R^3$ have the stated meaning and $R^5$ represents hydrogen, b) the 5-amino-1-hydroximoyl-pyrazole of the formula IV ($R^5$=H) is reacted with an aliphatic or aromatic sulphonyl chloride in the presence of a tertiary base with formation of the corresponding O-sulphonated 5-amino-1-hydroximoylpyrazole of the formula IV ($R^5$=-SO$_2$-R$^6$, in which $R^6$ represents an alkyl or aryl radical);

c) the O-sulphonated 5-amino-1-hydroximoyl-pyrazole is acylated at the amino group with formation of the corresponding O-sulphonated 5-acylamino- or 5-bisacylamino-1-hydroximoyl-pyrazole and then treated with bases.

An alkyl group represented by $R^1$ is for example methyl, ethyl, propyl, isopropyl, butyl, isobutyl, t-butyl, $C_5H_{11}$, $C_6H_{13}$, 2,4,4-trimethyl-pentyl, undecyl, $C_{13}H_{27}$, $C_{15}H_{31}$ or $C_{17}H_{35}$. Such alkyl groups may be substituted with, for example, alkoxy, aryloxy, amino, phthalimido, alkylsulphonyl or arylsulphonyl groups.

An aralkyl group represented by $R^1$ is for example benzyl, phenethyl or 3-phenylpropyl, wherein the phenyl group included therein may be further substituted by e.g. halo, alkoxy, nitro or acylamino groups.

An aryl group represented by $R^1$ or contained in a substituent $R^1$ is in particular phenyl, including substituted phenyl, e.g. phenyl substituted by alkyl, alkoxy or amino groups or chlorine.

A heterocyclic group represented by $R^1$ is for example thienyl.

In formulas I, II and IV, an alkyl group represented by $R^2$ is for example, methyl, ethyl, propyl, isopropyl, butyl, t-butyl, $C_5H_{11}$, $C_6H_{13}$, $C_{13}H_{27}$ or $C_{17}H_{35}$. Such alkyl groups may be substituted with, for example, alkoxy groups. A phenyl group represented by $R^2$ may be substituted with, for example, alkyl or alkoxy groups.

$R^3$ preferably represents hydrogen or chlorine.

An acyl radical represented by $R^4$ is derived for example from an optionally substituted alkanoic acid; acetyl, chloracetyl, and propionyl being examples.

The process may be performed by isolating the individual intermediate steps.

The following are examples of suitable starting compounds for the process according to the invention (3(5)-amino-pyrazoles of the formula II):
3(5)-amino-5(3)-methyl-pyrazole,
3(5)-amino-4-chloro-5(3)-methyl-pyrazole,
3(5)-amino-5(3)-tert.butyl-pyrazole,
3(5)-amino-4-chloro-5(3)-tert.butyl-pyrazole,
3(5)-amino-5(3)-ethoxy-pyrazole.

Examples of hydroximoyl halides which may be used are benzohydroximoyl chloride, benzohydroximoyl chlorides with substituents in the aromatic portion, as are described in J. Org. Chem. 45, 3916 (1980), as well as analogous synthesised aliphatic hydroximoyl halides, such as 3-phenyl-propanehydroximoyl chloride, 3-phthalimidopropanehydroximoyl chloride, 2-methyl-3-phthalimidopropanehydroximoyl chloride and 4-phthalimidobutanehydroximoyl chloride.

The reaction with the hydroximoyl halide of the general formula III is expediently performed in absolute aprotic solvents such as dioxan, acetonitrile or DMF. It may be carried out in such a way that, for example, the 3(5)-amino-pyrazole and a tertiary organic base, expediently triethylamine or pyridine, are introduced initially and are then treated, with thorough mixing, with a solution of the equimolar amount of the hydroximoyl halide. The temperature is preferably chosen to be between −10° and 40° C. After distilling off the solvent under vacuum, the 5-amino-1-hydroximoyl-pyrazole (formula IV with $R^5$=H) which is obtained may be further processed directly or may be purified e.g. by recrystallisation.

The compounds of the formula IV ($R^5$=H) prepared in this way are valuable intermediates for the preparation of pyrazolo[5,1-c][1,2,4]triazoles of the formula I. To process further, the compound of the formula IV ($R^5$=H) is sulphonated at the OH group in the hydroximoyl radical in an absolute aprotic solvent, such as absolute dioxan, acetonitrile, DMF or DMSO, with an organic sulphonyl chloride, e.g. with methanesulphonyl chloride, benzenesulphonyl chloride or 4-tosyl chloride in the presence of a tertiary base, preferably triethylamine or pyridine. Temperatures of −10° to 30° C. have proven to be suitable for this operation. Working-up may take place in various ways, by diluting with water, washing neutral, drying and concentrating by evaporation or simply by distilling off the solvent. The residue may be purified by recrystallisation. The product obtained (formula IV with $R^5$=alkyl- or arylsulphonyl) is then heated to 60° C. to 150° with a carboxylic acid anhydride such as acetanhydride, propionic anhydride or benzoic anhydride. If solvents are being used, it is advisable to use the carboxylic acid corresponding to the anhydride, such as acetic acid or propionic acid. After diluting with water or hydrolysing or distilling off the excess anhydride, the O-sulphonated 5-acylamino-1-hydroximoyl-pyrazoles are obtained. Acylation of the amino group may be catalysed by mineral acids such as sulphuric acid, hydrochloric acid or phosphoric acid, wherein two acyl groups may be introduced to give O-sulphonated 5-bisacylamino-1-hydroximoyl-pyrazoles. The O-sulphonated 5-acylamino-1-hydroximoyl-pyrazoles may be treated with a base in a solvent such as dioxan, acetonitrile, methanol, ethanol, DMF or DMSO. Bases which may advantageously be used are sodium methylate, sodium ethylate, or alcoholic solutions of sodium or potassium hydroxide, hydrazine or tertiary bases, e.g. DBU. The reaction temperature may be varied over wide limits, but for the most part is between 20° C. and 100° C. The de-acylated pyrazolo[5,1-c][1,2,4]triazoles (formula I, $R^4$=H) are obtained as the reaction products. On treatment with tertiary bases in aprotic solvents, the 1-acylpyrazolo[5,1-c][1,2,4]triazoles are formed, which are readily de-acylated under the action of alcoholic solutions of sodium or potassium hydroxide. Cyclisation of the O-sulphonated 5-bisacylamino-1-hydroximoyl-pyrazoles takes place using a methylate or ethylate solution or with an alcoholic solution of an alkali metal hydroxide or with hydrazine.

The 1-acyl-pyrazolo [5,1-c][1,2,4 ]triazoles and pyrazolo[5,1-c][1,2,4]triazoles are advantageously used as photographic colour coupler precursors or colour couplers.

EXAMPLE 1

6-methyl-3-(3-nitro-phenyl)pyrazolo[5,1-c][1,2,4]triazole

Synthesis step 1:

4.85 g (0.05 mol) of 3(5)-amino-5(3)-methyl-pyrazole in 50 ml of absolute dioxan are treated with 8.3 ml (0,06 mol) of triethylamine and then, under stirring at room temperature, are treated dropwise with a solution of 10 g (0.05 mol) of 3-nitro-benzohydroximoyl chloride in 50 ml of absolute dioxan. Stirring is continued for 3 hours and then the mixture is evaporated to dryness. The residue is treated with water and ethyl acetate. The organic phase is dried over magnesium sulphate, evaporated under vacuum and the residue obtained in this way is recrystallised from dioxan. 9.8 g (48%) of 5-amino-1-(3-nitro-benzohydroximoyl)-3-methyl-pyrazole with a m. pt. of 224° to 226° C. are obtained.

Synthesis step 2

7.4 g (0.028 mol) of 5-amino-1-(3-nitro-benzohydroximoyl)-3-methyl-pyrazole are treated in 90 ml of absolute acetonitrile with 4 ml (0.028 mol) of triethylamine and then, with stirring at room temperature, are treated dropwise with a solution of 5.55 g (0.029 mol) of 4-tosyl chloride in 150 ml of absolute acetonitrile. Stirring is continued for 1 hour and then the mixture is evaporated to dryness. The residue is treated with water and ethyl acetate, the organic phase is washed with water, dried over magnesium sulphate and evaporated under vacuum. The oily residue obtained in this way is crystallised from ethanol. 8.5 g (72%) of 5-amino-3-methyl-1-(O-tosyl-3-nitrobenzohydroximoyl)-pyrazole with a m. pt. of 156°–158° C. are obtained. The substance is light-sensitive. On recrystallising twice from ethanol, the m. pt. is 165°–169° C.

Synthesis step 3

2 g (4.8 mmol) of 5-amino-3-methyl-1-(O-tosyl-3-nitrobenzohydroximoyl)-pyrazole are heated for 5 minutes under reflux in 5 ml of acetanhydride. This is then cooled down and hydrolysed with water. The solid mass which forms after a little while is separated off, washed with water, dried in the air and recrystallised from acetonitrile. 1.9 g (86%) of 5-acetamido-3-methyl-1-(O-tosyl-3-nitrobenzohydroximoyl)-pyrazole with a m. pt. of 208°–212° C. (decomp.) are obtained.

Synthesis step 4

800 mg (1.75 mmol) of 5-acetamido-3-methyl-1-(O-tosyl-3-nitro-benzohydroximoyl)-pyrazole are suspended in 10 ml of DMSO, treated with 0.8 ml DBU with stirring at room temperature, diluted with water and acidified with 2N hydrochloric acid. The precipitate obtained is filtered under suction, washed with water, a little methanol and a little ethyl acetate and recrystallised from methyl glycol. 450 mg (90%) of 1-acetyl-6-methyl-3-(3-nitro-phenyl)pyrazolo[5,1-c][1,2,4]triazole with a m. pt. of 207°–210° C. are obtained.

Synthesis step 5

500 mg (1.75 mmol) of 1-acetyl-6-methyl-3-(3-nitro-phenyl)pyrazolo[5,1-c][1,2,4]triazole are mixed with 7 ml of methanol and 3 ml of 2N sodium hydroxide solution and heated at boiling point until a clear solution is produced, then cooled down and acidified with 2N hydrochloric acid. The precipitate formed is filtered off under suction, washed neutral with water and then washed with a little methanol and a little ethyl acetate. After recrystallisation from DMSO, 400 mg (94%) of 6-methyl-3-(3-nitro-phenyl)pyrazolo[5,1-c][1,2,4]triazole with a m. pt. of 269°–275° C. (decomposes from 247° C.) are obtained.

EXAMPLE 2

6-methyl-3-(2-phenyl-ethyl )pyrazolo[5, 1-c][1,2,4]triazole

Synthesis step 1

Analogous to example 1, synthesis step 1, using 5.65 g (0.058 mol) of 3(5)-amino-5(3)-methyl-pyrazole and 10.6 g (0.058 mol) of 3-phenyl-propanehydroximoyl chloride. The oil obtained as raw product is dissolved in nitromethane in the cold and made to crystallise by scratching the side of the container. 8.2 g (57%) of 5-amino-3-methyl-1-(3-phenyl-propanehydroximoyl)-pyrazole with a m. pt. of 138°–140° C. are obtained.

Synthesis step 2

Analogous to example 1, synthesis step 2, using 5 g (19.8 mmol) of 5-amino-3-methyl-1-(3-phenyl-propanehydroximoyl)-pyrazole. 3.9 g (49%) of semi-crystalline 5-amino-3-methyl-1-(3-phenyl-O-tosyl-propanehydroximoyl)-pyrazole are obtained and this is used for the next step.

Synthesis step 3

Analogous to example 1, synthesis step 3, using 2.9 g (7.25 mmol) of 5-amino-3-methyl-1-(3-phenyl-O-tosyl-propanehydroximoyl)-pyrazole crude product. After recrystallisation from acetonitrile, 1.5 g (47%) of 5-acetamido-3-methyl-1-(3-phenyl-O-tosyl-propanehydroximoyl)-pyrazole with a m. pt. of 141°–144° C. are obtained.

Synthesis step 4

1 g (2.27 mmol) of 5-acetamido-3-methyl-1-(3-phenyl-O-tosyl-propanehydroximoyl)-pyrazole mixed with 15 ml of methanol and 4 ml of 2N sodium hydroxide solution is stirred for 30 minutes at room temperature, when a clear solution is produced. The mixture is then adjusted to be weakly acid with conc. hydrochloric acid and the methanol is distilled off under vacuum, when a white precipitate is formed. The product may be recrystallised from nitromethane. 420 mg (82%) of 6-methyl-3-(2-phenyl-ethyl)pyrazolo[5,1-c][1,2,4]triazole with a m. pt. of 84°–185° C. are obtained.

EXAMPLE 3

3-(2-ammonio-1-methyl-ethyl)-6-tert.butyl-pyrazolo-[5,1-c][1,2,4 ]triazole tosylate Synthesis step 1

8.96 g (64.4 mmol) of 3(5)-amino-5(3)-tert.butyl-pyrazole in 100 ml of abs. dioxan are treated with 9.4 ml (67.6 mmol) of triethylamine and then under stirring treated dropwise over the course of 30 minutes with a solution of 20.56 g (77.2 mmol) of 2-methyl-3-phthalimido-propanehydroximoyl chloride in 100 ml of abs. dioxan. The reaction temperature rises from 20° C. to 32° C. Stirring is continued for 15 minutes, precipitated triethylamine hydrochloride is removed by filtering under suction, the filtrate is evaporated to dryness under vacuum at a maximum temperature of 40° C. and the residue obtained in this way is ground up with a little methanol, whereupon crystallisation takes place. The crystals are filtered off under suction and washed with a little methanol. 16.56 g (70%) of 5-amino-3-tert.butyl-1-(2-methyl-3-phthalimido-propanehydroximoyl)-pyrazole with a m. pt. of 198°–199° C. are obtained.

Synthesis step 2

Analogous to example 1, synthesis step 2, using 21.9 g (59.3 mmol) of 5-amino-3-tert.butyl-1-(2-methyl-3-phthalimido-propanehydroximoyl)-pyrazole, 10.5 ml (75.5 mmol) of triethylamine and 14.25 g (75.1 mmol) of 4-tosyl chloride. Working-up takes place by filtering off the precipitated triethylamine hydrochloride, evaporating the filtrate under vacuum, dissolving the residue in ethyl acetate, washing the organic phase three times with water, drying the organic phase over magnesium sulphate and evaporating at a maximum temperature of 40° C. The non-crystalline residue is dissolved in 200 ml of acetanhydride and heated at boiling point for 15 minutes. Then the excess acetanhydride is recovered by vacuum distillation. The residue is dissolved in 50 ml of hot methanol and allowed to stand for 3 hours to crystallise. 23.4 g (70%) of 5-acetamido-3-tert.butyl-1-(2-methyl-3-phthalimido-O-tosyl-propanehydroximoyl)-pyrazole with a m. pt. of 170°–172° C. are obtained.

Synthesis step 3

1.00 g (1.8 mmol) of 5-acetamido-3-tert.butyl-1-(2-methyl-3-phthalimido-O-tosyl-propanehydroximoYl)-pyrazole mixed with 20 ml of ethanol and 1 ml of hydrazine hydrate (80 %) are heated under reflux for 10 minutes. On cooling, phthalic hydrazide separates out and is filtered off under suction and washed with a little ethanol. The filtrate is evaporated to dryness, taken up in 10 ml of water and heated for 1 hour under reflux, after the addition of 100 mg of 5% palladium on charcoal to decompose excess hydrazinc hydrate. After filtering off the catalyst, this is evaporated to dryness under vacuum and the residue boiled with nitromethane. 0.50 g (71%) of 3-(2-ammonio-1-methyl-ethyl )-6-tert.butyl-pyrazolo[5, 1-c]triazole tosylate with a m. pt. of 216°–220° C. are obtained.

EXAMPLE 4

3-(2-ammonio-ethyl)-6-tert. butyl-pyrazolo [5,1-c][1,2,4 ]triazole tosylate

Synthesis step 1

Analogous to example 1, synthesis step 1, using 1.01 g (7.3 mmol) of 3(5)-amino-5(3)-tert.butyl-pyrazole and 2.0 g (ca. 7.9 mmol) of 3-phthalimido-propanehydroximoyl chloride crude product (m. pt. 155°–171° C.). The reaction product, which is produced as a resin (purified by flash chromatography, m. pt. 80°–82° C.), in 4 ml of absolute acetonitrile, is treated with 0.4 ml triethylamine and then, with stirring, 0.53 g (2.8 mmol) of 4-tosyl chloride is added dropwise. This is allowed to react for 1 hour, precipitated triethylamine hydrochloride is filtered off under suction and washed with a little ethyl acetate, the combined filtrate is evaporated to dryness and the amorphous residue is ground up with a little methanol, when crystallisation occurs. 0.75 g (21%) of 5-amino-3-tert.butyl-1-(3-phthalimido-O-tosyl-propanehydroximoyl)pyrazole with a m. pt. of 168°–172° C. are obtained.

Synthesis step 2

4.39 g (8.6 mmol) of 5-amino-3-tert.butyl-1-(3-phthalimido-O-tosyl-propanehydroximoyl)pyrazole are reacted with acetanhydride in the same way as in example 1, synthesis step 3. The crude product which is obtained is recrystallised from methanol. 2.8 g (59%) of 5-acetamido-3-tert.butyl-1-(3-phthalimido-O-tosyl-propanehydroximoyl)-pyrazole with a m. pt. of 195°–201° C. are obtained.

Synthesis step 3

Analogous to example 3, synthesis step 3, using 2.49 g (4.5 mmol) of 5-acetamido-3-tert.butyl-1-(3-phthalimido-O-tosyl-propanehydroximoyl)-pyrazole and 2.5 ml 80% strength hydrazine hydrate. Decomposition of excess hydrazinc hydrate was performed using Raney nickel. 1.0 g (63%) of 3-(2-ammonio-ethyl)-6-tert.butyl-pyrazolo[5,1-c]-[1,2,4]triazole tosylate with a m. pt. of 231°–240° C. were obtained.

EXAMPLE 5

3-[2-(2-carboxy-benzamido)ethyl ]-7-chloro-6-methyl-pyrazolo[5,1-c][1,2,4]triazole Synthesis step 1

Analogous to example 3, synthesis step 1, using 1.2 g (9.1 mmol) of 3(5)-amino-4-chloro-5(3)-methyl-pyrazole and 2.3 g (9.1 mmol) of 3-phthalimido-propanehydroximoyl chloride in dioxan. Working up is performed in such a way that after separating the triethylamine hydrochloride, the liltrate is evaporated to dryness under vacuum and the oily residue diluted with methanol. A crystalline precipitate (ca. 780 mg) of the nitrile oxide dimers of the hydroximoyl chloride which is produced as a side product forms and this is separated off. The methanolic mother liquor is evaporated to dryness. 2.67 g of an oil is obtained which is dissolved in 12 ml absolute acetonitrile, treated with 1.1 ml (7.9 mmol) of triethylamine and then, dropwise at room temperature, with a solution of 1.47 g (7.7 mmol) of 4-tosyl chloride in 5 ml of absolute acetonitrile. This is left to react for 10 minutes, evaporated to dryness under vacuum and the oily residue is ground up with methanol. The ground up with methanol. The crystals obtained in this way are separated off and washed with a little methanol. 1.36 g (30%) of 5-amino-4-chloro-3-methyl-1-(3-phthalimido-O-tosyl-propanehydroximoyl)-pyrazole with a m. pt. of 168°–171° C. are obtained.

Synthesis step 2

2.62 g (5.2 mmol) of 5-amino-4-chloro-3-methyl-1-(3-phthalimido-O-tosyl-propanehydroximoyl)pyrazole in 15 ml of acetanhydride, to which 0.15 ml of concentrated sulphuric acid has been added, are heated to boiling point and then cooled down. After careful hydrolysis the solid obtained is ground up with methanol and boiled in methanol. The crystals which are produced are filtered off under suction and washed with a little methanol. 1.44 g (47%) of 5-bisacetylamino-4-chloro-3-methyl-1-(3-phthalimido-O-tosyl-propanehydroximoyl)pyrazole with a m. pt. of 143°–147° C. are obtained.

Synthesis step 3

380 mg (0.65 mmol) of 5-bisacetylamino-4-chloro-3-methyl-1-(3-phthalimido-O-tosyl-propanehydroximoyl)pyrazole, mixed with 15 ml methanol and 15 ml of 2N sodium hydroxide solution, are heated under reflux for 10 minutes. The solution is then filtered, neutralised and freed of methanol under vacuum. The crystals which precipitate from the aqueous solution are separated off and washed with water. They may be recrystallised from a 1:1 water/ethanol mixture. 110 mg (49%) of 3-[2-[2-carboxy-benzamido)ethyl]-7-chloro-6-methyl-pyrazolo[5,1-c][1,2,4]triazole with a m. pt. of 162°–166° C. are obtained.

What is claimed is:

1. A 5-amino-1-hydroximoyl-pyrazole of the formula IV,

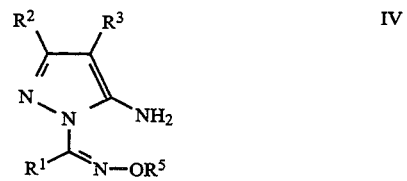

in which $R^1$ represents an optionally substituted alkyl, aralkyl or aryl radical;

$R^2$ represents an optionally substituted alkyl radical;

$R^3$ represents hydrogen or chlorine; and $R^5$ represents hydrogen or an alkyl- or arylsulphonyl radical.

* * * * *